United States Patent
Taylor et al.

[11] Patent Number: 6,143,694
[45] Date of Patent: Nov. 7, 2000

[54] NON-AUXIN PREHARVEST CURING AIDS FOR TOBACCO

[76] Inventors: John B. Taylor, 1420 Lemon St., Deland, Fla. 32720; Elmo B. Whitty, 13815 Millhopper Rd., Gainesville, Fla. 32653; Merrill Wilcox, 2911 NW. 30th Ter., Gainesville, Fla. 32605

[21] Appl. No.: 09/228,024

[22] Filed: Jan. 9, 1999

Related U.S. Application Data

[60] Provisional application No. 60/020,977, Jan. 9, 1998.

[51] Int. Cl.[7] .......................... A01N 43/54; A01N 43/66; A01N 43/42; A01N 43/40; A01N 43/48
[52] U.S. Cl. .......................... 504/227; 504/239; 504/243; 504/247; 504/251; 504/253; 504/277
[58] Field of Search ...................... 504/212, 277, 504/253, 247, 227, 251, 243, 239

[56] References Cited

U.S. PATENT DOCUMENTS

| | | | |
|---|---|---|---|
| 4,851,029 | 7/1989 | Durr et al. | 71/90 |
| 5,188,657 | 2/1993 | Hamprecht et al. | 504/212 |

FOREIGN PATENT DOCUMENTS

| | | |
|---|---|---|
| 284 419 | 9/1988 | European Pat. Off. |
| 375 875 | 7/1990 | European Pat. Off. |

*Primary Examiner*—Jose' G. Dees
*Assistant Examiner*—Alton Pryor
*Attorney, Agent, or Firm*—Merrill Wilcox

[57] ABSTRACT

A method of aiding in ripening and curing tobacco by application to the tobacco plant of an effective amount of a compound selected from a group comprising imidazolinones; sulfonylureas; triazolopyrimidinesulfonanilides; and pyrimidinylthiobenzoic acids and related compounds.

29 Claims, No Drawings

NON-AUXIN PREHARVEST CURING AIDS FOR TOBACCO

This appln claims the benefit of Provisional Appln 60/020,977 filed Jan. 9, 1998.

BACKGROUND OF THE INVENTION

1. Field of the Invention

The successful, profitable growing of tobacco (*Nicotiana tabacum* L.) requires great skill at judging the proper stage for various decisions and taking such action in a timely manner. Flue-cured tobacco is the most important segment of the total crop in the United States. Tobacco must reach a particular level of maturity before it is harvested. A tobacco leaf is considered mature when among other characteristics, the lamina (i. e. leaf blade area between veins) begins to develop a slight yellow color. The tobacco leaves are removed, either mechanically or by hand, from the stalk in sequential harvests and each pass consists of three to six leaves. There will usually be a total of 16 to 22 harvestable leaves per stalk. Flue-cured leaf is cured by being subjected to artificial heating and ventilation in a barn especially designed for that purpose. The first step of the curing process is to further develop the yellow color of the leaf, which requires about three days, or half of the normal curing period. If the tobacco has not reached the correct level of maturity before being harvested and put in the barn, the tobacco will not cure properly and will lose market value. Barn capacity is one of the larger costs to the grower; therefore most growers do not have an excess of barn capacity. Heating fuel used to cure the tobacco is also a major cost to the grower. Therefore to have a profitable operation, the grower must harvest the tobacco at maximum ripeness to conserve fuel, and the grower must allow his tobacco to ripen in accordance with a schedule that allows a barn to always be available when tobacco is ripe enough for harvest. However for efficient utilization, the barns should be used for as many curings per season as possible. Tobacco ripens best when water and nutrients are much less available in the soil after all leaves are fully expanded. Consequently, ripeness may be particularly delayed by excess nitrogen and moisture, and to a lesser extent by other nutrients in the soil, as the tobacco crop approaches the projected harvest date.

As our agricultural production has become more intensified, these uncertainties relating to maturity have been addressed by various means; of particular interest are preharvest curing aids which have been developed, which are described in E. B. Whitty, et al., 1992, *Enforcement Procedures Result in Label Compliance in Use of Chemicals for Yellowing Tobacco, Proceedings of Soil and Crop Science Society of Florida*, Vol. 52, pp. 14–17, which is hereby incorporated by reference in its entirety. These developments have allowed the tobacco grower to exert greater control over time of harvest and time of placing the crop in the barn for curing. This has allowed more efficient use of fuel and barn capacity. The compound 2-chlorethylphosphonic acid is the only commercial product labeled by the EPA and in use for this purpose. Possible disadvantages of 2-chlorethylphosphonic acid are that effective use requires about 500 grams per acre or more and many tobaccos are reduced in market quality by the usual change to a more orange color that it produces. Another possible disadvantage of 2-chlorethylphosphonic acid is that it is perhaps an alkylating agent. The 1992 Whitty reference also describes the illegal (in the sense that they were used not in accordance with their EPA labels) use of various synthetic auxin herbicides as preharvest curing aids at rates of 250 to 500 grams per acre. From the standpoint of label compliance it is unfortunate that these synthetic auxin herbicides produce a more natural appearing ripening of the tobacco, both in the field and after curing in the barn than does 2-chlorethylphosphonic acid. An important disadvantage of the synthetic auxin herbicides as preharvest curing aids is that they produce to varying degrees epinasty of the treated leaves. Epinasty is more vigorous growth of the upper leaf surface relative to the lower leaf surface, with resultant puckering and malformation of the leaf; it is characteristic and diagnostic of both synthetic and natural auxins. This epinasty is always quite apparent to the grower. Tobacco growers are normally very traditional and very conservative. Tobacco growers would find this epinasty associated with the use of synthetic auxins quite unacceptable, even though there is no intrinsic problem with curing such treated leaf; it turns out very high quality tobacco from the barn after curing. Massive education efforts would probably be necessary to convince growers to accept these synthetic auxins as preharvest curing aids for tobacco.

The methods for preharvest curing aids to be disclosed in this application are advantageous over the prior art 2-chloroethylphosphonic acid methods in that the treated leaf is much more natural in appearance and could be expected to develop into cured leaf earning a much higher price in the market. The compounds of the new methods also require a much lower application rate than prior art 2-chloroethylphosphonic acid and unlike 2-chloroethylphosphonic acid, are clearly not alkylating agents. The methods for preharvest curing aids to be disclosed in this application are advantageous over the prior art illegal (i. e., used out of label) synthetic auxin herbicide methods in that the treated leaf is much more natural in appearance and could be expected to develop into cured leaf earning an unusually high price in the market. This is because the new methods do not produce leaf epinasty and would be immediately accepted by the typical conservative, traditional tobacco grower. The methods for preharvest curing to be disclosed in this application are also advantageous over the prior art methods in that they require a much lower application rate than prior art illegal (i. e., used out of label) synthetic auxin herbicide methods.

2. Related Art

The related art is well described in E. B. Whitty, et al., 1992, *Enforcement Procedures Result in Label Compliance in Use of Chemicals for Yellowing Tobacco, Proceedings of Soil and Crop Science Society of Florida*, Vol. 52. pp. 14–17, which has been incorporated by reference in its entirety. There is no prior art reference to the compounds useful in this invention as preharvest curing aids for tobacco.

SUMMARY OF THE INVENTION

A method of aiding in curing and ripening of tobacco wherein curing and ripening are induced by preharvest application to the tobacco plant of an effective amount of a compound selected from a group comprising imidazolinones, sulfonylureas, triazolopyrimidinesulfonanilides, and pyrimidinylthiobenzoic acids and related compounds.

DETAILED DESCRIPTION OF THE INVENTION

Preharvest curing aids useful in the methods of the present invention are selected members of the triazolopyrimidinesulfonanilide and pyrimidinylthio(optionally oxy)benzoic acid families, and more preferably, selected members of the imidazolinone and sulfonylurea families. These are unexpected new methods in the disclosed uses of these compounds described herein. The triazolopyrimidinesulfonanilide family, the pyrimidinylthio(optionally oxy)benzoic, the sulfonylurea, and the imidazolinone families have never had reports nor even speculation of utility as preharvest curing aids for tobacco.

These compounds have a common biochemical mechanism in that they inhibit the first step used by plants to synthesize the amino acids valine, leucine and isoleucine. The enzyme involved is known as acetolactate synthase (ALS is the generally preferred term), or as acetohydroxyacid synthase (AIS). The process is also described as branched-chain amino acid biosynthesis. The attributes of these compounds are described in some detail in a symposium entitled "Herbicides Inhibiting Branched-Chain Amino Acid Biosynthesis" at the 194th national meeting of the American Chemical Society, Aug. 30–Sep. 4, 1987 in New Orleans, La., U.S.A. This symposium was hosted by Moberg and Cross, and published in Pesticide Science, Volume 29, page 241, 1990 which is hereby incorporated by reference.

Imidazolinones which are useful in the methods of this invention are disclosed in the following three U.S. patents, all of which are hereby incorporated by reference:

1. In U.S. Pat. No. 4,798,619, Example 42, columns 103–104 and preceding, is described the synthesis of 2-[4, 5-dihydro-4-methyl-4-(1-methylethyl)-5-oxo-1H-imidazol-2-yl]-3-quinolinecarboxylic acid, which has the common name imazaquin; in this same patent in Example 18, columns 79–80, are described the syntheses of 2-[4,5-dihydro4-methyl-4-(1-methylethyl)-5-oxo-1H-imidazol-2-yl]-=5-ethyl-3-pyridinecarboxylic acid, which has the common name imazethapyr, and also of ±-2-[4,5-dihydro4methyl-4-(1-methylethyl)-5-oxo-1H-imidazol-2-yl]-5-methyl-3-pyridinecarboxylic acid which has the common name imazameth; and in Example 10, columns 70–71, is described the synthesis of ±-2[4,5-dihydro-4methyl-4-(1-methylethyl)-5-oxo-1H-imidazol-2-yl]-3-pyridinecarboxylic acid, which has the common name imazapyr.

2. In U.S. Pat. No. 4,188,487, columns 3–5, is described the synthesis of ±-2-[4,5-dihydro-4-methyl-4-(1-methylethyl)-5-oxo-1H-imidazol-2-yl]-4(and 5)-methylbenzoic acid (3:2) which has the common name imazamethabenz; in the same patent in Example 2, columns 8–10, is described the synthesis of the methyl ester of imazamethabenz.

3. In U.S. Pat. No. 5,334,576, columns 6–9, is described the synthesis of +-5-methoxymethyl-2-[4,5-dihydro-4-methyl-4-(1-methylethyl)-5-oxo-1H-imidazol-2-yl]-3-pyridinecarboxylic acid, which has the common name imazamox.

These imidazolinones described in the above three patents are extremely useful in the methods of this invention. The tobacco treated at very low application rates with these curing aids does not differ in any detectable way from naturally cured tobacco of the highest quality, and is particularly desirable.

Sulfonylureas which are useful in the methods of this invention are disclosed in the following 19 U.S. patents, all of which are hereby incorporated by reference:

1. In U.S. Pat. No. 4,671,819, Example H3, column 12, is described the synthesis of 1-(4-methoxy-6-methyltriazin-2-yl)-3-[2-(3,3,3-trifluoropropyl)-phenylsulfonyl]-urea, which has the common name prosulfuron.

2. In U.S. Pat. No. 4,514,212, Example 2c, columns 9–10, is described the synthesis of 2-(2-chloroethoxy)-N-[4-methoxy-6-methyl-1,3,5-triazin-2-yl)amino]carbonyl] benzenesulfonamide, which has the common name triasulfuron; synthetic methods in this same patent may be used for the preparation of 3-(4,6-dimethoxy-1,3,5-triazin-2-yl)-1-[2-(2-methoxyethoxy)-phenylsulfonyl]urea, which has the common name cinosulfuron.

3. In U.S. Pat. No. 4,478,635, Example 2c, column 10, is described the synthesis of methyl 2-[[[[[4,6-bis (difuoromethoxy)-2-pyrimidinyl]amino]carbonyl]amino] sulfonyl]benzoate, which has the common name primisulfuron.

4. In U.S. Pat. No. 4,394,506, Example 3, column 21, is described the synthesis of methyl 2-[[[[(4,6-dimethyl-2-pyrimidinyl)amino]carbonyl]amino]sulfonyl]benzoate, which has the common name sulfometuron.

5. In. U.S. Pat. No. 4,547,215, Example 2, column 3, is described the synthesis of ethyl 2-[[[[(4-chloro-6-methoxy-2-pyrimidinyl)amino]carbonyl]amino]sulfonyl]benzoate, which has the common name chlorimuron.

6. In U.S. Pat. No. 5,209,771, columns 3 and 4, is described the synthesis of 2-[[[[(4,6-dimethyl-2-pyrimidinyl)amino]carbonylamino]sulfonyl]benzoic acid, 3-oxetanyl ester, which has the common name oxasulfuron.

7. In U.S. Pat. No. 4,383,113, Example 13, columns 44–45, is described the synthesis of methyl 2-[[[[(4-methoxy-6-methyl-1,3,5-triazin-2-yl)amino]carbonyl] amino]sulfonyl]benzoate, which has the common name metsulfuron.

8. In U.S. Pat. No. 4,548,638, Example 1, column 4, is described the synthesis of methyl 2-[[[[[4-ethoxy-6-(methylamino)-1,3,5-triazin-2-yl]amino]carbonyl]amino] sulfonyl]benzoate, which has the common name ethametsulfuron.

9. In U.S. Pat. No. 4,740,234, Example 1, column 2, is described the synthesis of methyl 2-[[[[(4-methoxy-6-methyl-1,3,5-triazin-2-yl)methylamino]carbonyl]amino] sulfonyl]benzoate, which has the common name tribenuron.

10. In U.S. Pat. No. 4,789,393, Example 9, columns 11–12, is described the synthesis of 2-[[[[(4,6 ethoxy-2-pyrimidinyl)amino]carbonyl]amino]sulfonyl]-N,N-dimethyl-3-pyridinecarboxamide, which has the common name nicosulfuron; in this same patent are methods that may be used to synthesize 1-(4,6-dimethoxypyrimidin-2-yl)-3-[3-(trifluoromethyl)-2-pyridylsulfonyl]urea, which has the common name flazasulfuron; and also to synthesize 2-chloro-N-[[(4,6-dimethoxy-2-pyrimidinyl)=amino] carbonyl]imidazo[1,2-a]pyridine-3-sulfonamide, which has the common name imazosulfuron.

11. In U.S. Pat. No. 4,127,405, Example 3, column 8, is described the synthesis of 2-chloro-N-[(4-methoxy-6-methyl-1,3,5-triazin-2-yl)aminocarbonyl] benzenesulfonamide, which has the common name chlorsulfuron.

12. In U.S. Pat. No. 4,420,325, Examples 14–16, columns 13–16, is described the synthesis of methyl 2-[[[[(4,6-dimethoxy-2-pyrimidinyl)amino]carbonyl]amino]sulfonyl] methyl]benzoate, which has the common name bensulfuron.

13. In U.S. Pat. No. 5,090,933, Example 6, column 9, is described the synthesis of methyl 2-[[[[[4-(dimethylamino)-6-(2,2,2-trifluoroethoxy)-1,3,5-triazin-2-yl]amino] carbonyl]amino]=sulfonyl]-3-methylbenzoate, which has the common name triflusulfuron.

14. In U.S. Pat. No. 5,492,884, column 2, is described the synthesis of [[[[[(4,6-dimethoxy-2-pyrimidinyl)amino]

carbonyl]amino]sulfonyl]amino]-2-(cyclopropylcarbonyl)-4-fluorobenzene, which has the common name cyclosulfamuron.

15. In U.S. Pat. No. 4,746,353, columns 14–20, is described the synthesis of N-[[(4,6-dimethoxy-2-pyrimidinyl)amino]carbonyl]-1-methyl-4-(2-methyl-2H-tetrazol-5-yl)-1H-pyrazole-5-sulfonamide, which has the common name azimsulfuron.

16. In U.S. Pat. No. 4,668,277, Example 2, columns 5–6, is described the synthesis of methyl 5-[[(4, 6-dimethoxy-2-pyrimidinyl)aminocarbonylaminosulfonyl]-3-chloro-1-methyl-1-H-pyrazole-4-carboxylate, which has the common name halosulfuron; in this same patent are set forth methods that may be used to synthesize 5-(4,6-dimethoxypyrimidin-2-ylcarbamoylsulfamoyl)-1-methylpyrazole-4-=carboxylic acid, which has the common name pyrazosulfuron.

17. In U.S. Pat. No. 5,102,444, columns 13–14 and 31–32 is described the synthesis of N-((4,6-dimethoxypyrimidin-2-yl)aminocarbonyl)-3-(3-ethylsulfonyl)-2-pyridinesulfonamide, which has the common name rimsulfuron.

18. In U.S. Pat. No. 5,017,212, columns 21–24, 28–31, 35–36, 39–42, 65–66 and 71–72, is described the synthesis of N-(2-ethylsulfonylimidazo[1,2-a]pyridin-3-ylsulfonyl)-N'-(4,6-dimethoxy-=2-pyrimidinyl)urea, which has the common name sulfosulfuron.

19. In U.S. Pat. No. 4,481,029, columns 14–20, is described the synthesis of methyl 3-[[[[(4-methoxy-6-methyl-1,3,5-triazin-2-yl)amino]carbonyl]amino]sulfonyl]-2-thiophenecarboxylate, which has the common name thifensulfuron.

These sulfonylureas described in the above 19 patents are extremely useful in the methods of this invention. The tobacco treated at very low application rates with these curing aids does not differ in any detectable way from naturally cured tobacco of the highest quality, and is particularly desirable.

Triazolopyrimidinesulfonanilides which are useful in the methods of this invention are disclosed in the following two U.S. patents, both of which are hereby incorporated by reference:

1. In U.S. Pat. No. 4,954,163, columns 7–21 is described the synthesis of N-(2,6-difluorophenyl)-5-methyl[1,2,4]triazolo[1,5-α]pyrimidine-2-sulfonamide, which has the common name flumetsulam, and also of N-2,6-dichloro-3-methylphenyl)-5,7-dimethoxy[1,2,4]triazolo[1,5a]pyrimidine-2-sulfonamide, which has the common name metosulam.

2. In U.S. Pat. No. 4,893,772, columns 23–24 and preceding, and in the above U.S. Pat. No. 5,954,163, columns 7–21, are described methods suitable for the synthesis of N-(2-carbomethoxy-6-chloro=phenyl)-5-ethoxy-7-fluoro[1,2,4]triazolo[1,5c]pyrimidine-2-sulfonamide, which has the common name chloransulam-methyl.

3. In U.S. Pat. No. 5,163,995, columns 5–9, is described the synthesis of N-(2,6-dichlorophenyl)-5-ethoxy-7-fluoro[1,2,4]triazolo-[1,5-c]pyrimidine-2-sulfonamide, which is known by the provisional name XDE-564.

These triazolopyrimidinesulfonanilides have utility in the methods of the present invention. These triazolopyrimidinesulfonanilides are very effective in the methods of the present invention.

Pyrimidinylthio(or optionally oxy)benzoic compounds, which are useful in the methods of this invention are disclosed in the following two U.S. patents, both of which are hereby incorporated by reference:

1. In U.S. Pat. No. 4,923,501, Example 2, is described the synthesis of 2-chloro-6-[(4,6-dimethoxy-2-pyrimidinyl)thio]benzoic acid, which has the common name pyrithiobac.

2. In U.S. Pat. No. 4,932,999, Example 1, is again described the synthesis of 2-chloro-6-[(4,6-dimethoxy-2-pyrimidinyl)thio]benzoic acid, which has the common name pyrithiobac. These pyrimidinylthio(or optionally oxy) benzoic acids and related compounds, as exemplified by pyrithiobac, have utility in the methods of this invention. These pyrimidinylthio(or optionally oxy)benzoic acids and related compounds are very effective in the methods of the present invention.

The active substances of this invention are not phytotoxic in the usual application concentrations in these methods, and they have low toxicity towards warm-blooded animals. They moreover produce no morphological changes of the plants nor cause damage to them. They promote, in particular, the ripening and yellowing of tobacco so as to make the tobacco cure more rapidly and to better quality when put in the barn.

The extent and nature of the action are governed by the most diverse factors, depending on the type of plant, on the applied concentration and on the time of application with regard to the stage of development of the plant. The active substances preferably are applied in the form of liquid preparations, over the top of the tobacco plant one to two weeks before the normal expected harvest date. One skilled in the art may make many modifications within the concept of this invention.

The active substances of this invention may be used together with suitable carriers, solvents and/or other additives, or in many cases as formulated by the manufacturer. Suitable adjuvants are Silwet L-77, a non-ionic silicone-polyether copolymer adjuvant and X-77, a similar non-ionic adjuvant, both distributed by Loveland Industries, Inc. Regulaid, distributed by Kalo, Inc. is also suitable. Any one of these is suitable in aqueous solution of 0.025–0.05% adjuvant applied at forty to eighty gallons per acre. One skilled in the art can substitute other adjuvants with acceptable results. Suitable carriers and additives can be solid or liquid, and correspond to the substances normally used in formulation practice, for example, solvents, dispersing agents, wetting agents, other surfactants, adhesives and thickening or bonding agents. Most conveniently, the formulations will be prepared in concentrated forms to which water can be added to produce the solutions and slurries described above. As used herein, the term "carrier" refers to all of the solvents, diluents, surfactants, etc., comprising the subject formulations, other than the active imidazolinone, sulfonylurea, triazolopyrimidinesulfonanilide, or pyrimidinylthio(optionally oxy)benzoic acid ingredient.

The applied amounts are largely governed by the purpose and nature of the application. The usual rates of treatment applied over the tops of the tobacco plants are 2 to 130 grams active ingredient per acre in 20 to 100 gallons of carrier per acre. The carrier may be either aqueous solution or slurry. It is preferable that the application not exceed incipient runoff. It is preferable, for environmental and other reasons, to use the subject compounds in as low application rates as possible. Therefore, it is preferable to employ application rates below 100 grams active ingredient per acre if possible and more preferable to employ application rates below 60 grams active ingredient per acre. These application rates are unusually low, and therefore environmentally desirable as they produce less burden of extraneous compounds in the environment. It has been found that suitable application rates for the sulfonylureas and pyrimidinylthio(optionally oxy)benzoic acids are from 2 to 20 grams active ingredient per acre, with a rate of about 10 grams active ingredient per acre being especially preferred. For the imidazolinones and triazolopyrimidinesulfonanilides the preferred rates are somewhat higher, namely in the range of 40 to 70 grams active ingredient per acre with a rate of about 50 grams active ingredient per acre being especially preferred. The optimum time of application to promote ripening and curing is from one to two weeks before the projected harvest date.

EXAMPLES 1–7

The test compounds as commercially formulated were applied at the indicated rates in grams active ingredient per acre in the specified volume of aqueous 0.05% Silwet L-77 (a non-ionic adjuvant, a silicone-polyether copolymer distributed by Loveland Industries, Inc.) per acre. The treatments and a control of the carrier solution alone were applied over the top of K-326 or other varieties of tobacco plants, set in the field at the rate of 7500–7700 plants per acre, about two weeks before expected harvest. One to two weeks after treatment, the upper leaves were rated from one to ten for ripeness, one equaling negligible ripening, two through four equaling various levels of partial ripening, five equaling the threshold of sufficient ripeness for immediate harvest into the barn, and 10 equaling maximum ripening:

Example 1

The test compounds were applied to variety K-326 tobacco plants in 43 gallons of carrier per acre. One week after treatment, the upper leaves were rated for ripeness.

| Compound | Grams active ingredient per acre | Rating of ripeness |
| --- | --- | --- |
| Triasulfuron | 25 | 10 |
| Primisulfuron | 25 | 10 |
| Sulfometuron | 15 | 10 |
| Oxasulfuron | 30 | 7 |
| Pyrithiobac | 30 | 8 |
| Bensulfuron | 30 | 6 |
| Thifensulfuron | 40 | 8 |
| Carrier control | 0 | 1 |

Example 2

The test compounds were applied in 43 gallons of carrier per acre. Ten days after treatment, the upper leaves were rated for ripeness.

| Compound | Grams active ingredient per acre | Rating of ripeness |
| --- | --- | --- |
| Sulfometuron | 15 | 6 |
| Metsulfuron | 10 | 9 |
|  | 20 | 10 |
| Nicosulfuron | 20 | 4 |
|  | 40 | 4 |
| Chlorsulfuron | 20 | 4 |
|  | 40 | 4 |
| Tribenuron | 20 | 6 |
|  | 40 | 6 |
| Rimsulfuron | 20 | 4 |
| Cyclosulfamuron | 20 | 3 |
| Carrier control | 0 | 1 |

Example 3

The test compounds were applied in 43 gallons of carrier per acre. One week after treatment, the upper leaves were rated for ripeness.

| Compound | Grams active ingredient per acre | Rating of ripeness |
| --- | --- | --- |
| Prosulfuron | 20 | 5 |
| Halosulfuron | 20 | 5 |
| Pyrithiobac | 30 | 5 |
|  | 45 | 6 |
| Chloransulam methyl | 30 | 6 |
|  | 45 | 8 |
| Carrier control | 0 | 2 |

Example 4

The test compounds were applied to variety K-326 tobacco plants in 43 gallons of carrier per acre. One week after treatment, the upper leaves were rated for ripeness.

| Compound | Grams active ingredient per acre | Rating of ripeness |
| --- | --- | --- |
| Prosulfuron | 25 | 5 |
| Triasulfuron | 25 | 8 |
| Primisulfuron | 25 | 8 |
| Sulfometuron | 15 | 9 |
| Oxasulfuron | 30 | 10 |
| Halosulfuron | 30 | 10 |
| Chlorimuron | 25 | 10 |
| Pyrithiobac | 30 | 10 |
| Bensulfuron | 30 | 6 |
| Thifensulfuron | 40 | 8 |
| Triflusulfuron | 40 | 7 |
| Sulfosulfuron | 40 | 6 |
| Carrier control | 0 | 1 |

Example 5

The test compounds were applied in 43 gallons of carrier per acre. Ten days after treatment, the upper leaves were rated for ripeness.

| Compound | Grams active ingredient per acre | Rating of ripeness |
| --- | --- | --- |
| Prosulfuron | 10 | 5 |
|  | 20 | 7 |
| Triasulfuron | 10 | 5 |
|  | 20 | 7 |
| Primisulfuron | 10 | 5 |
|  | 20 | 7 |
| Sulfometuron | 10 | 4 |
|  | 15 | 8 |
| Oxasulfuron | 10 | 4 |
|  | 20 | 6 |
| Halosulfuron | 10 | 4 |
|  | 20 | 6 |
| Chlorimuron | 10 | 5 |
|  | 20 | 7 |
| Pyrithiobac | 10 | 5 |
|  | 20 | 6 |
| Bensulfuron | 10 | 5 |
|  | 20 | 5 |
| Thifensulfuron | 10 | 4 |
|  | 20 | 4 |

-continued

| Compound | Grams active ingredient per acre | Rating of ripeness |
| --- | --- | --- |
| Triflusulfuron | 10 | 4 |
|  | 20 | 3 |
| Cyclosulfamuron | 10 | 3 |
|  | 20 | 3 |
| Carrier control | 0 | 1 |

Example 6

The test compounds were applied in 43 gallons of carrier per acre. One week after treatment, the upper leaves were rated for ripeness.

| Compound | Grams active ingredient per acre | Rating of ripeness |
| --- | --- | --- |
| Imazaquin | 30 | 3 |
|  | 45 | 3 |
|  | 60 | 5 |
|  | 90 | 4 |
| Imazethapyr | 30 | 5 |
|  | 45 | 3 |
|  | 60 | 6 |
|  | 90 | 7 |
| Imazamethabenz methyl | 30 | 3 |
|  | 45 | 3 |
|  | 60 | 4 |
|  | 90 | 4 |
| Imazapyr | 30 | 5 |
|  | 45 | 6 |
|  | 60 | 8 |
| Imazameth | 30 | 5 |
|  | 45 | 6 |
|  | 60 | 9 |
| Imazamox | 30 | 4 |
|  | 45 | 4 |
|  | 60 | 7 |
|  | 90 | 8 |
| Carrier control | 0 | 1 |

Example 7

Applying the following preharvest curing aids as described in Example 2 should result in the great majority of the tobacco leaves receiving a rating of ripening of five or above, thus allowing their immediate placement in the curing barn:

| Compound | Grams active ingredient per acre |
| --- | --- |
| Flumetsulam | 50 |
| Metosulam | 50 |
| Azimsulfuron | 35 |
| Ethametsulfuron | 35 |
| Flazasulfuron | 40 |
| Imazosulfuron | 35 |
| Pyrazosulfuron | 40 |
| Cinosulfuron | 35 |

Example 8

Two replications of formulated metsulfuron are applied at 7.5 grams per acre in 50 gallons of water carrier which contains one ml of various adjuvants per gallon. One week after treatment, the upper leaves are rated for ripeness as described in examples 1–7.

| Adjuvant | Rating of ripeness |
| --- | --- |
| X-77 | 8.0 |
| Regulaid | 8.3 |
| L-77 | 8.3 |
| Carrier control | 1.0 |

DESCRIPTION OF THE PREFERRED EMBODIMENT

Flue-cured tobacco that is about two weeks prior to normal harvest is treated over the top with formulated metsulfuron at the rate of 7.5 grams of active ingredient per acre in a carrier of 50 gallons of 0.05% aqueous X-77 per acre. One week later, the crop is ripe for harvest and immediate curing in the barn.

We claim:

1. A method of aiding in the ripening of a tobacco plant wherein ripening is induced by preharvest application to the tobacco plant of an effective but non-phytotoxic amount of a compound:

2-[4,5-dihydro-4-methyl-4-(1-methylethyl)-5-oxo-1H-imidazol-2-yl]arylcarboxylate, wherein the arylcarboxylate is selected from a group comprising quinolin-3-$COOR^1$, $R^2$-benzene-$COOR^1$, and 5-$R^3$-pyridine-3-$COOR^1$; $R^1$ is H, $CH_3$, ammonium, or lower alkylamine, $R^2$ is 4-$CH_3$ or 5-$CH_3$, $R^3$ is H, $CH_3$, $CH_2CH_3$, or $CH_2OCH_3$.

2. The method of claim 1 wherein imazaquin or a salt thereof is applied to the tobacco plant.

3. The method of claim 1 wherein imazethapyr or a salt thereof is applied to the tobacco plant.

4. The method of claim 1 wherein imazapyr or a salt thereof is applied to the tobacco plant.

5. The method of claim 1 wherein imazameth or a salt thereof is applied to the tobacco plant.

6. The method of claim 1 wherein imazamethabenz or a salt or methyl ester thereof is applied to the tobacco plant.

7. The method of claim 1 wherein imazamox or a salt thereof is applied to the tobacco plant.

8. A method of aiding in the ripening of a tobacco plant wherein ripening is induced by preharvest application to the tobacco plant of an effective but non-phytotoxic amount of a sulfonylurea:

$QNHCONHSO_2W$, where if Q is 4-methoxy-6-methyl-triazin-2-yl, W is 2-$R^4$-phenyl, and $R^4$ is 3,3,3-trifluoropropyl, 2-chloroethoxy, chloro, or methoxycarbonyl;

where if Q is 4-$R^5$-6-$R^6$-triazin-2-yl, W is 6-$R^7$-2-methoxycarbonylphenyl, $R^5$ is ethoxy or 2,2,2-trifluoroethoxy, $R^6$ is methylamino or dimethylamino, and $R^7$ is hydrogen or methyl.

9. The method of claim 8, wherein prosulfuron is applied to the tobacco plant.

10. The method of claim 8 wherein triasulfuron is applied to the tobacco plant.

11. The method of claim 8 wherein metsulfuron is applied to the tobacco plant.

12. The method of claim 8 wherein clorsulfuron is applied to the tobacco plant.

13. The method of claim 8 wherein tribenuron is applied to the tobacco plant.

14. The method of claim 8 wherein triflusulfuron is applied to the tobacco plant.

15. The method of claim 8 wherein ethametsulfuron is applied to the tobacco plant.

16. The method of claim 8 wherein pyrazosulfuron is applied to the tobacco plant.

17. The method of claim 8 wherein cinosulfuron is applied to the tobacco plant.

18. A method of aiding in the ripening of a tobacco plant wherein ripening is induced by preharvest application to the tobacco plant of an effective but non-phytotoxic amount of a sulfonylurea:

$$XNHCONHSO_2Y,$$

where if X is 4-methoxy-6-methyl-pyrimidin-2-yl, Y is 3-$R^8$-pyridin-2-yl, and $R^8$ is dimethylaminocarbonyl; or Y is 4-methoxycarbonyl-3-chloro-1-methyl-1H-pyrazole-5-, 1-methyl-4-(2-methyl-2H-tetrazol-5-yl)pyrazole-5-, or 2-cyclopropoxycarbonylphenylamino;

where if Y is 2-$R^9$-phenyl, and $R^9$ is a carbonyl group substituted with ethoxy-, methoxy-, or 3-oxetanyloxy-, X is 4-$R^{10}$-6-$R^{11}$-pyrimidin-2-yl, where $R^{10}$ is chloro, methyl, methoxy, or difluoromethoxy, and $R^{11}$ is methyl, methoxy, or difluoromethoxy;

where if X is 4,6-dimethoxypyrimidin-2-yl, Y is 3-ethylsulfonylpyridin-2-yl, or 2-ethylsulfonylimidazo[1,2-a]pyridin-3-yl.

19. The method of claim 18 wherein rimsulfuron is applied to the tobacco plant.

20. The method of claim 18 wherein sulfosulfuron is applied to the tobacco plant.

21. The method of claim 18 wherein nicosulfuron is applied to the tobacco plant.

22. The method of claim 18 wherein azimsulfuron is applied to the tobacco plant.

23. The method of claim 18 wherein primisulfuron is applied to the tobacco plant.

24. The method of claim 18 wherein sulfometuron is applied to the tobacco plant.

25. The method of claim 18 wherein oxasulfuron is applied to the tobacco plant.

26. The method of claim 18 wherein chlorimuron is applied to the tobacco plant.

27. The method of claim 18 wherein bensulfuron is applied to the tobacco plant.

28. The method of claim 18 wherein cyclosulfamuron is applied to the tobacco plant.

29. The method of claim 18 wherein halosulfuron is applied to the tobacco plant.

* * * * *